United States Patent [19]
Costello, Jr. et al.

[11] Patent Number: 5,348,646
[45] Date of Patent: Sep. 20, 1994

[54] FLUID FILTER ASSEMBLY

[76] Inventors: John R. Costello, Jr., 3169 Gove Dr., Tecumseh, Mich. 49286; Leonard F. Knoedler, 5119 Pontiac Trail, Ann Arbor, Mich. 48105; Monty E. Vincent, 3575 Miller Rd., Ann Arbor, Mich. 48103; Mary K. Boomus, 13829 Riker Rd., Chelsea, Mich. 48108

[21] Appl. No.: 976,964

[22] Filed: Nov. 16, 1992

[51] Int. Cl.5 .............................................. B01D 65/10
[52] U.S. Cl. ...................................... 210/94; 210/436
[58] Field of Search .................. 210/647, 436, 472, 94

[56] References Cited

U.S. PATENT DOCUMENTS

| | | | |
|---|---|---|---|
| 3,905,905 | 9/1975 | O'Leary et al. | 210/436 |
| 4,009,714 | 3/1977 | Hammer | 128/214 R |
| 4,111,807 | 9/1978 | Boomus et al. | 210/152 |
| 4,190,426 | 2/1980 | Ruschke | 210/436 X |
| 4,319,996 | 3/1982 | Vincent et al. | 210/188 |
| 4,369,112 | 1/1983 | Vincent et al. | 210/433.2 |
| 4,906,260 | 3/1990 | Emheiser et al. | 210/436 X |
| 4,995,268 | 2/1991 | Ash et al. | 210/647 |
| 5,252,222 | 10/1993 | Matkovich et al. | 210/436 X |

FOREIGN PATENT DOCUMENTS

| | | |
|---|---|---|
| 0007547 | 6/1980 | European Pat. Off. . |
| 0061328 | 9/1982 | European Pat. Off. . |
| 0302722 | 3/1988 | European Pat. Off. . |
| 0489403 | 3/1991 | European Pat. Off. . |
| 1401382 | 7/1975 | United Kingdom . |
| 2134812 | 8/1984 | United Kingdom . |

*Primary Examiner*—Frank Spear
*Attorney, Agent, or Firm*—Reising, Ethington, Barnard, Perry & Milton

[57] ABSTRACT

A filter assembly (10) includes a hollow housing (12) having a length and first and second ends (14,16). A membrane (22) contained within and extending along the length of the housing (12) separates the housing (12) into first and second chambers (24,26). An inlet (32) is proximate to the first end (14) and is in fluid communication with the first chamber (24). An outlet (34) is proximate to the second end (16) and is in fluid communication with the second chamber (26) for allowing a flow of fluid from the second chamber (26). The membrane (22) is air permeable when dry and air impermeable when wet whereby a wetting fluid entering the first chamber (24) at the first end of the housing (12) forces air from the first and second chambers (24,26) along the length of the membrane (22) and out of the outlet (34) as the fluid wets the membrane (22) thereby de-airing the first and second chambers (24,26) from one end to the other end along the length of the membrane (22) on both sides thereof.

9 Claims, 1 Drawing Sheet

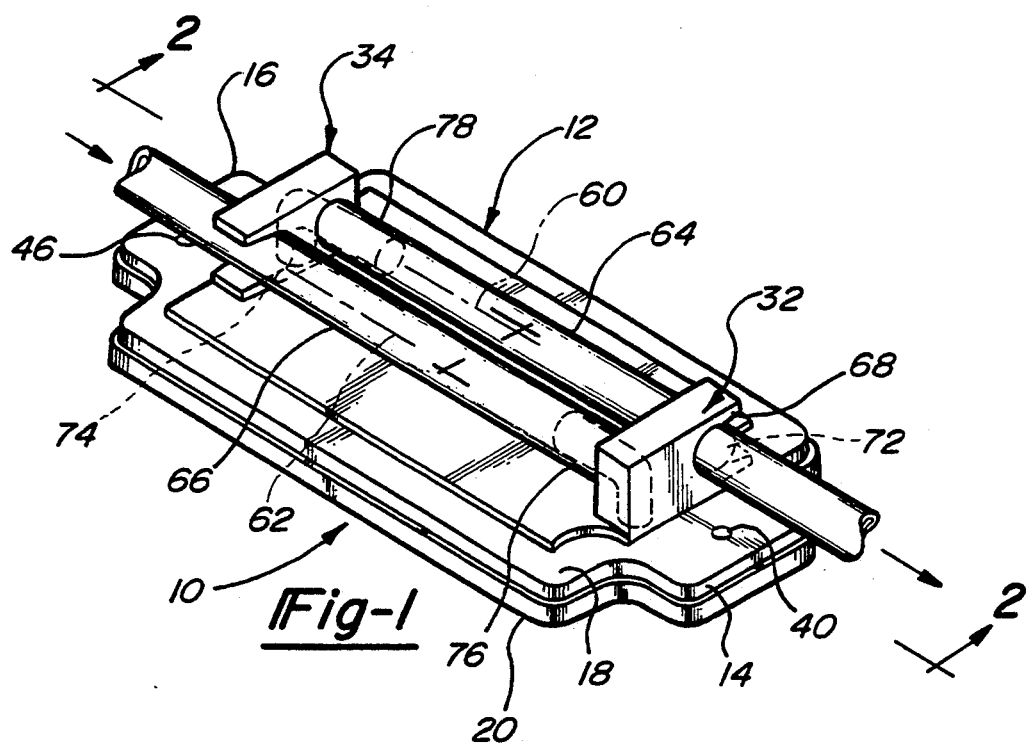
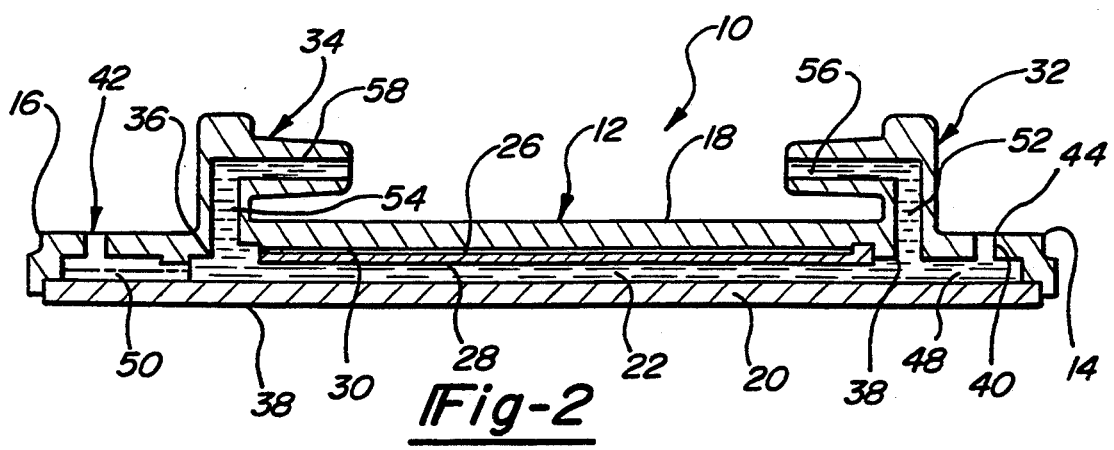

FLUID FILTER ASSEMBLY

TECHNICAL FIELD

This invention relates to a fluid filter device, with particular utility for filtering liquids administered intravenously and requiring removal of particulates and air from the fluids.

BACKGROUND ART

It is common practice to filter various kinds of liquids when the liquids are administered by an intravenous unit to a patient. Generally, the liquid is passed through a filter housing containing a flat microporous hydrophilic membrane sealed to the walls of the filter housing and supported by a grid or the like.

It is also well known that when a hydrophilic membrane is wet (that is, when the pores are filled with the liquid being filtered), air or other gas cannot pass through the membrane except under increased pressure. Hence, if there is air or other gas in the liquid being filtered, it accumulates on the inlet surface of a membrane and blocks or interferes with the passage of liquid through the membrane. It is also necessary to prevent the air from flowing in the liquid to the patient. Therefore, it is necessary to remove the air, as well as other particulates, from the liquid while also removing the air from the filter housing.

With specific regard to initiating the intravenous fluid flow, most systems require various manipulations to simultaneously prime the filter housing with the liquid while removing air that is trapped within the filter housing on the inlet side and outlet side of the membrane.

Additionally, it is quite useful to determine whether or not air remains trapped in a filter housing during liquid flow through the housing.

The U.S. Pat. Nos. 4,111,807 to Boomus et al., issued Sep. 5, 1978; 4,319,996 to Vincent et al., issued Mar. 16, 1982; and 4,369,112 to Vincent et al., issued Jan. 18, 1983, all relate to various filter assemblies for use in intravenous administration settings. Each of these assemblies do not include any means for allowing simple priming of the assembly to remove air therefrom, nor do they provide any means for simply and readily indicating air remaining in the system once liquid is flowing therethrough.

SUMMARY OF THE INVENTION AND ADVANTAGES

In accordance with the present invention, there is provided a filter assembly including a hollow housing having a length and first and second ends. Membrane means extends along the length of the housing and separates the housing into first and second chambers. Inlet means proximate to the first end and in fluid communication with the first chamber allows a flow of fluid into the first chamber. Outlet means proximate to the second end and in fluid communication with the second chamber allows flow of the fluid from the second chamber, the membrane means being air permeable when dry and air impermeable when wet. Thusly, a wetting fluid entering the first chamber at the first end of the housing forces air from the first and second chambers along the length of the membrane means and out of the outlet means as fluid wets the membrane means along the length thereof thereby de-airing the first and second chambers from one end to the other end along the length of said membrane means on both sides thereof.

BRIEF DESCRIPTION OF THE DRAWINGS

Other advantages of the present invention will be appreciated as the same becomes better understood by reference to the following detailed description when considered in connection with the accompanying drawings wherein:

FIG. 1 is a perspective view of a housing with a filter assembly made in accordance with the present invention; and FIG. 2 is a cross-sectional view taken along lines 2—2 of FIG. 1.

DETAILED DESCRIPTION OF THE INVENTION

A filter assembly made in accordance with the present invention is generally shown at 10 in the figures. The filter assembly includes a housing generally shown at 12, the housing having a length extending from a first end 14 to a second end 16. The housing 12 is preferably made from two housing halves 18,20, the two housing halves 18,20 defining two walls 18,20 of the housing.

The housing halves 18,20 can be connected together by means well known in the art such as by gluing, sonic welding, or any other fusion-type bonding, but not limited to these methods.

A hydrophilic membrane 22, as shown in FIG. 2, is contained within and extends along the length of the housing 12 and separates the housing 12 into first and second chambers 24,26. The membrane 22 is seated on a grid support 28 of a type well-known in the art. For example, the grid support 28 can be projections or the like extending from an inner surface 30, the projections or the like allowing fluid flow through the second chamber 26. The membrane 22 is mounted on the inner surface 30 of the first wall 18 about its periphery by means well know in the art. For example, the periphery of the membrane 22 can be either heat sealed, glued, or the like to a mounting surface about the periphery of the membrane 22. Such means of connecting membranes to filter housing walls are well known in the art.

The filter assembly 10 includes an inlet generally indicated at 32 proximate to the first end 14 of the housing 12, the inlet 32 being in fluid communication with the first chamber 24 for allowing the flow of fluid into the first chamber 24. An outlet is generally shown at 34 as being proximate to the second end 16 of the housing 12 and in fluid communication with the second chamber 26 for allowing a flow of fluid from the second chamber 26 out of the housing 12.

The membrane 22 is a hydrophilic microporous membrane and, as such, is air permeable when dry and air impermeable when wet. A wetting fluid entering the first chamber 24 at the first end 14 of the housing forces air from the first and second chambers 24,26 along the length of the membrane 22 and out the outlet 34 as the fluid wets the membrane 22 thereby de-airing the first and second chambers 24,26 from one end to the other end along the length of the membrane 22 on both sides thereof. That is, upon initially using the filter assembly 10, there is a requirement that the air be removed from the entirety of the first and second chambers 24,26 as well as from the inlet and outlets 32,34. This is accomplished as the filter assembly 10 is primed with the liquid to be administered intravenously to a patient.

The disposition of the inlet 32 and outlet 34 at each end of the first chamber 24 and second chamber 26, respectively, in combination with the membrane 22 being air permeable when dry creates a fluid circuit whereby as the liquid to be administered enters the inlet 32 and flows to one side of the membrane 22 in the first chamber 24, the liquid forces air towards the second end 16 of the housing 12 and also towards the outlet 34. Simultaneously, the air is forced through the remaining dry portions of the membrane 22 ahead, or upstream, of the head of the fluid flow. Simultaneously, the fluid wets and permeates the membrane 22 to likewise force air from the first end 14 of the housing 12 on the other side of the membrane 22 in the second chamber 26 towards the second end 16 of the housing 12. As this is done, the head of the liquid flow through the second chamber 26 also forces air out through the outlet 34. Thusly, simultaneously, air is being forced towards the outlet 34 in both the first chamber 24 and the second chamber 26 as the system is primed with the liquid to be administered. Thusly, the filter assembly 10 is de-aired from one end to the other along the length of the membrane 22 on both sides thereof in a totally passive manner requiring no other manipulations of the assembly, no matter what the orientation of the assembly is, relative to the patient.

More specifically, the membrane 22 is a flat-sheet, hydrophilic, microporous membrane. The membrane can have pore sizes between 0.1 and 5.0 microns. Examples of such membranes are polysulfone, acrylic copolymers, cellulosic, polyethersulfone, and hydrophilic polyolefin.

The inlet 32 and the outlet 34 extend 10 through a first wall 18 defined by the first housing half. As described above, the membrane 22 extends between the first and second walls 18,20 defining the first and second chambers 24,26. The membrane 22 is operatively connected to the first wall 18 as described above and extends along the length thereof and over the outlet opening 36, as shown in FIG. 2. The membrane 22 extends to a point adjacent to the inlet opening 38 and is sealed therefrom whereby the inlet opens through the first wall 18 and is in direct fluid communication with the first chamber 24 which extends between the membrane 22 and the second wall 20. Likewise, the outlet opening 36 opens through the first wall 18 and is in fluid communication with the second chamber 26. In this manner, the assembly 10 is oriented such that it has a totally flat surface 38 on one side thereof which facilitates mounting on a patient's limb or the like.

The first chamber 24 extends along the length of the housing 12 to the ends 14,16 thereof beyond the inlet and outlet 32,34. The assembly 10 includes air vent means generally indicated at 40 and 42, extending through the housing 12 between the ends 14,16 of the housing 12 and each of the respective inlet and outlet 32,34 for venting air from the fluid flowing from the inlet 32 before and after the membrane 22 is wetted and becomes air impermeable. That is, once the membrane 22 is wetted, air flowing in with the wetting liquid cannot pass through the wetted membrane 22. Since the flow of the wetting fluid from the inlet into the chamber 24 not only flows into the chamber but flows along the length of the membrane, air trapped within the first chamber 22 is necessarily forced towards the first and second ends 14,16 of the housing. The air vent means 40,42 allows for venting of the air being forced to the ends of the first chamber 24 by the flow of the wetting liquid through the first chamber 24. Thusly, the assembly 10 passively and automatically de-airs itself during wetting liquid flow therethrough.

More specifically, the air vent means 40,42 each include a port 44,46, respectively, extending through the first wall 18 adjacent each end 14,16 thereof. A hydrophobic membrane 48,50 is mounted over each of the ports 44,46, respectively. More specifically, the membrane is a flat sheet, hydrophobic, microporous membrane. The membrane can have pore sizes between 0.01 and 0.03 micron. Examples of such membranes are PTFE and polyolefin. The membranes are mounted by connection of their peripheries to the inner surface 30 of the first wall 18 by methods known in the art, described above, such as heat welding or the like.

The inlet 32 and outlet 34 each include an L-shaped passageway including a respective first portion 52,54 extending through the first wall 18 and a respective second portion 56,58 extending along the length of the housing 12. The second portion 56 of the inlet 32 opens toward the opening of the second portion 58 of the outlet 34, with each of the second portions 56,58 defining a line 60,62, as shown in FIG. 1, extending along the length thereof. Each line 60,62 is spaced from and parallel to the other.

The assembly 10 includes retaining means adjacent to each of the first portions 52,54 of the passageways extending through each of the inlet and outlet 32,34. The retaining means extend over the lines 60,62 defined by the opposite second passageways 56,58 of the inlet and outlet 32,34 for retaining a tube 64 mounted on and extending from the inlet 32 by the retaining means adjacent the outlet 34 and retaining a tube 66 mounted on and extending from the outlet 34 adjacent to the inlet 32. More specifically, each retaining means includes a substantially C-shaped portion 68,70 extending from the first wall 18 adjacent to the first portions 52,54 of the passageways of the inlets and outlets 32,34. As shown in FIG. 1, these C-shaped portions have an inner surface 72,74 defining a channel, the channels of each of the C-shaped portions 72,74 being parallel relative to each other. Thusly, the orientation of the inlet and outlet 32,34 in combination with the C-shaped portions 72,74 allow for tubes extending from the inlet and outlet 32,34 to be parallel and clamped such that if the device is taped to a limb, the tape can extend over the tubings and simultaneously secure the device to the patient's limb while securing the tubings relative to the assembly 10.

As discussed above, it is desirable to be able to determine whether air is inadvertently trapped within the housing of a filter device. The housing 12 of the present invention includes air indicative means for indicating when air is contained within the housing 12 as a wetting fluid is flowing therethrough. More specifically, the walls 18,20 are substantially transparent and have a frosted inner surface 30,31. A wetting fluid will cause the walls 18,20 to appear transparent as the wetting fluid adjacent the frosted walls will clearly transmit light therethrough. When air is adjacent the frosted surfaces 30,31, the air adjacent the walls 18,20 will cause the walls 18,20 to appear translucent, thereby indicating air to be existent in the housing 12. Thusly, the present invention provides means for indicating air within any type of filter device having walls made in accordance with the present invention, that is, the walls being substantially transparent and having a frosted inner surface.

In use, an inlet tube 64 is first connected to the mounting portion 76 of the inlet 32. The tube 64 is secured within the C-shaped portion 70 adjacent the outlet 34. Fluid enters from the tube 64 into the inlet 32. The fluid will force air out through the air vent 40 and also through the first chamber 24. Air will exit through the air vent 42, as well as through the membrane 22 ahead of the fluid stream until the membrane is wetted thereby. Simultaneously, as the fluid wets the membrane 22 and passes therethrough, the fluid will force air from the second chamber 28 and out through the outlet 34 by the continuous flow of fluid until the tube 66 is de-aired and then can be connected to either a catheter or other mounting as desired.

The invention has been described in an illustrative manner, and it is to be understood the terminology used is intended to be in the nature of description rather than of limitation.

Obviously modifications and variations of the present invention are possible in light of the above teachings. Therefore, it is to be understood that within the scope of the appended claims, wherein reference numerals are merely for convenience and are not to be in any way limiting, the invention may be practiced otherwise than as specifically described.

We claim:

1. A filter assembly (10) comprising:

a hollow housing (12) having a length and first and second ends (14, 16);

membrane means (22) contained within and extending along said length of said housing (12) and separating said housing (12) into first and second chambers (24,26);

inlet means (32) proximate to said first end (14) and in fluid communication with said first chamber (24) for allowing a flow of fluid into said first chamber (24); and outlet means (34) proximate to said second end (16) and in fluid communication with said second chamber (26) for allowing a flow of fluid from said second chamber, (26) said membrane means (22) being air permeable when dry and air impermeable when wet, whereby a wetting fluid entering said first chamber (24) at said first end of said housing (12) forces air from said first and second chambers (24, 26) along said length of said membrane means (22) and out said outlet means (34) as the fluid wets said membrane means (22) thereby de-airing said first and second chambers (24, 26) from one end to the other end along the length of said membrane means (22) on both sides thereof, said inlet and outlet means (32, 34) each including an L-shaped passageway including a first portion (52, 54) extending perpendicular to the length of said membrane means and a second portion (56, 58) extending along said length of said housing (12), said second portion (56) of said inlet means 32 opening towards said opening of said second portion (58) of said outlet means (34), each of said second portions (56, 58) defining a line (60, 62) extending along the length thereof and each of said lines (60, 62) being spaced from and parallel to the other of said lines (60, 62).

2. A filter assembly of claim 1 wherein said membrane means is a flat-sheet, hydrophilic, microporous membrane.

3. A filter assembly of claim 2 wherein said housing includes a first wall (18) and an opposite second wall, said inlet and outlet means (32,34) extending through said first wall (18), said membrane means (22) extending between said first and second walls (18,20), defining said first and second chambers (24,26), said membrane means (22) being operatively connected to said first wall (18) and extending along a length thereof and over said outlet means (34) and adjacent to said inlet means (32) and being sealed from said inlet means (32) whereby said inlet means (32) extends through said first wall and is in direct fluid communication with said first chamber (24) which extends between said membrane means (22) and said second wall (20) and said outlet means (34) extends through said first wall (18) and is in fluid communication with said second chamber (26).

4. A filter assembly of claim 3 wherein said first chamber (26) extends along said length of said housing (12) to said first and second ends (14,16) thereof beyond said inlet and outlet means (32,34), said assembly including air vent means (40,42) extending through said housing (12) between said first and second ends (14,16) of said housing (12) and each of said respective inlet and outlet means (32,34) for venting air from the fluid flowing from said inlet (32) before and after said membrane means (22) is wetted and becomes air impermeable.

5. A filter assembly of claim 4 wherein said air vent means includes a port (44,46) extending through said first wall (18) adjacent each of said first and second ends (14,16) thereof and a hydrophobic membrane (48,50) mounted over each of said ports (44,46).

6. A filter assembly of claim 1 including tube retaining means adjacent to each of said first portions (52,54) of said passageways and extend over said line (60,62) defined by the opposite second passageway (56,58) of said inlet and outlet means (32,34) for retaining a tube (64) mounted on and extending from said inlet means (22) by said retaining means adjacent said outlet means (34) and retaining a tube (66) mounted on and extending from said outlet means (34) adjacent to said inlet means (32).

7. A filter assembly of claim 6 wherein said retaining means includes a substantially C-shaped portion (68,70) extending from said first wall (18) adjacent to said first portion of said passageways of said inlet and outlet means (32,34).

8. A filter assembly of claim 1 wherein said housing (12) includes air indicator means for indicating where air is contained within said housing (12) as a wetting fluid is flowing therethrough.

9. A filter assembly of claim 8 wherein said first and second walls (18,20) are substantially transparent and have frosted inner surfaces whereby a wetting fluid causes said first and second walls (18,20) to appear transparent and air adjacent said first and second walls (18,20) cause said first and second walls (18,20) to appear translucent thereby indicating air in said housing (12).

* * * * *